United States Patent [19]

Stack et al.

[11] Patent Number: 5,126,366
[45] Date of Patent: Jun. 30, 1992

[54] AMINOPHENOXYALKYL DERIVATIVES OF BENZODIOXAN

[75] Inventors: Gary P. Stack, Ambler; Magid A. Abou-Gharbia, Glen Mills; Terrance H. Andree, Doylestown, all of Pa.; Noreen T. Scherer, Plainsboro, N.J.

[73] Assignee: American Home Products Corporation, New York, N.Y.

[21] Appl. No.: 719,887

[22] Filed: Jun. 21, 1991

[51] Int. Cl.⁵ ............... A61K 31/335; C07D 319/20
[52] U.S. Cl. ...................... 514/452; 549/366; 549/361; 549/349; 548/950; 548/526; 546/197; 540/596; 540/480; 514/450; 514/422; 514/321; 514/218; 514/212
[58] Field of Search ............ 549/366, 361, 349; 548/950, 526; 546/197; 540/596, 480; 514/452, 450, 422, 321, 218, 212

[56] References Cited

U.S. PATENT DOCUMENTS

| | | | |
|---|---|---|---|
| 2,695,295 | 11/1954 | Swain | 549/366 |
| 2,725,386 | 11/1955 | Bovet et al. | 549/366 |
| 3,170,933 | 2/1965 | Schmidt | 549/366 |
| 3,324,143 | 6/1967 | Moed et al. | 549/366 |
| 4,684,739 | 8/1987 | Kikumoto et al. | 549/366 |
| 5,010,078 | 4/1991 | Abou-Gharbia et al. | 514/252 |
| 5,036,070 | 7/1991 | Abou-Gharbia | 514/252 |

FOREIGN PATENT DOCUMENTS

| | | |
|---|---|---|
| 170213 | 2/1986 | European Pat. Off. |
| 236930 | 9/1987 | European Pat. Off. |
| 57-142972 | 9/1982 | Japan |
| 58-219114 | 12/1983 | Japan |
| 6407012 | 12/1964 | Netherlands |

OTHER PUBLICATIONS

Indian J. Chem., Sect. B., 1982, 21B(10), 914–918.
Fozard, et al., Br. J. Pharmacol. 90, 273P (1987).
Banno et al. C. A., 96:854343 (1982)

Primary Examiner—Nicky Chan
Attorney, Agent, or Firm—Richard K. Jackson

[57] ABSTRACT

The compounds:

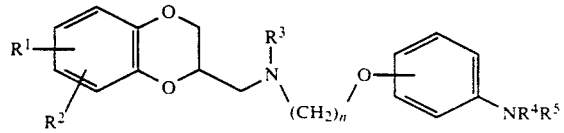

wherein $R^1$ and $R^2$ are, independently, hydrogen, alkyl, alkoxy, aralkoxy, alkanoyloxy, hydroxy, amino, mono- or dialkylamino, alkanamido, or sulfonamido, or $R^1$ and $R^2$ together form methylenedioxy, ethylenedioxy, or propylenedioxy; $R^3$ is hydrogen or alkyl; n is one of the integers 2, 3 or 4; $R^4$ and $R^5$ are, independently, hydrogen, alkyl, cycloalkyl, alkanoyl, aroyl, alkylsulfonyl or arylsulfonyl, or $R^4$ and $R^5$ together form a 3-7 membered polymethylene ring; or a pharmaceutically acceptable salt thereof, are antipsychotic, antidepressant and anxiolytic agents useful in the treatment of multi-CNS disease states.

19 Claims, No Drawings

AMINOPHENOXYALKYL DERIVATIVES OF BENZODIOXAN

BACKGROUND OF THE INVENTION

Indian J. Chem., Sect B 1982, 21B(10), 914-18 discloses a series of (aminophenoxy)(arylpiperazinyl)propanes (I) with potent CNS depressant, hypotensive, α-adrenoceptor blocking, antiinflammatory, and diuretic activities. The compound in which $RHN=p-NH_2$ and $R^1=o-MeO$ is a potent neuroleptic.

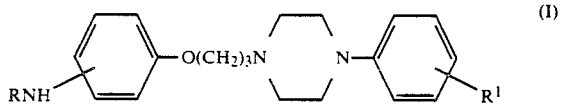

Jpn. Kokai Tokkyo Koho JP 57,142,972 and Fr. Demande FR 2,477,542 claim compounds of formula (II) as antihistaminic, anti-aggressive, and adrenaline antagonistic agents, useful as central nervous system agents. R is H, alkyl, phenylalkyl, alkenyl, alkynyl; Z is N-phenylimino, (un)substituted benzylidene; n is 0 or 1; $Z^1$ is alkylene; and $Z^2$ is CO, CH(OH), (un)substituted vinylene or ethylene.

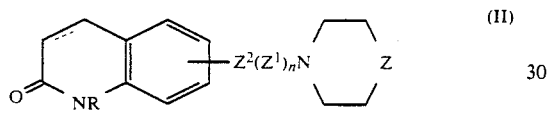

European Patent Application EP 170,213 discloses a series of glutarimide derivatives of benzodioxan methanamine as antianxiety and antihypertensive agents. Fozard et. al. Br. J. Pharmacol. 90, 273P (1987) disclose 8-[4-(1,4-benzodioxan-2-ylmethylamino)butyl]-8-azaspiro[4.5]decane-7,9-dione (MDL 72832) as a selective and stereospecific [(−)-MDL 72832 binds 32 times as much as the dextrorotary isomer at the $5-HT_{1A}$ receptor site] ligand for $5-HT_{1A}$ receptors.

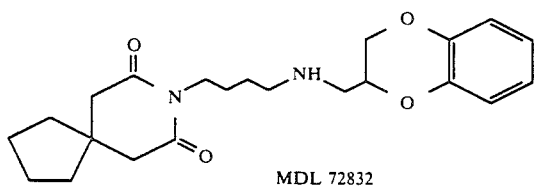

MDL 72832

European Patent EP 236,930 discloses a series of 2-substituted-alkyl-1,2-benzisothiazole-3-one 1,1-dioxide derivatives useful as anxiolytic and antihypertensive agents. Specifically claimed is 2-(4-(2,3-dihydro-1,4-benzodiox-2-yl)methylamino)butyl)-1,2-benzisothiazol-3(2H)-one 1,1-dioxide.

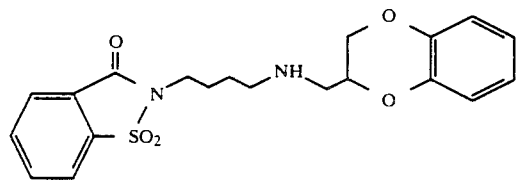

Neth 6,407,012 claims compounds of general formula (III), in which R, R1 and R2 are H, halogen, (1-6C) alkyl, or (1-6C) O-alkyl and n is an integer 2-6, as calming, hypnotic and hypotensive agents. Preferred among these structures are compounds in which $R^1$ and $R^2$ are oxygen-containing substituents. Jpn. Kokai Tokkyo Koho JP 58,219,114 claims similar compounds in which the two oxygen substituents in the phenoxy moiety are joined by a methylene, ethylene, or propylene bridge.

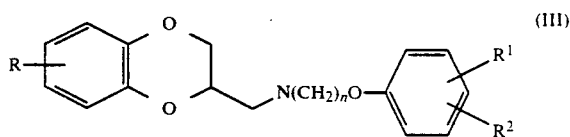

DESCRIPTION OF THE INVENTION

In accordance with this invention, there is provided a group of novel antipsychotic agents of the formula:

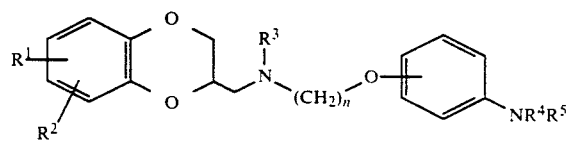

wherein
$R^1$ and $R^2$ are, independently, hydrogen, alkyl of 1 to 6 carbon atoms, alkoxy of 1 to 6 carbon atoms, aralkoxy of 7 to 12 carbon atoms, alkanoyloxy of 2 to 6 carbon atoms, hydroxy, halo, amino, mono- or dialkylamino in which each alkyl group contains from 1 to 6 carbon atoms, alkanamido of 2 to 6 carbon atoms, or sulfonamido, or $R^1$ and $R^2$ together form methylenedioxy, ethylenedioxy, or propylenedioxy;
$R^3$ is hydrogen or alkyl of 1 to 6 carbon atoms;
n is one of the integers 2, 3 or 4;
$R^4$ and $R^5$ are, independently, hydrogen, alkyl of 1 to 6 carbon atoms, cycloalkyl of 4 to 7 carbon atoms, alkanoyl of 2 to 6 carbon atoms, aroyl of 7 to 12 carbon atoms, alkylsulfonyl of 1 to 6 carbon atoms or arylsulfonyl of 6 to 10 carbon atoms, or $R^4$ and $R^5$ together form a 3-7 membered polymethylene ring;
or a pharmaceutically acceptable salt thereof.

Of these compounds, the preferred members are those in which $R^1$ and $R^2$ are hydrogen, fluoro, hydroxy, alkoxy of 1 to 6 carbon atoms or alkanoyloxy of 2 to 6 carbon atoms, or together form a methylenedioxy, ethylenedioxy or propylenedioxy ring; $R^4$ and $R^5$ are hydrogen or alkyl of 1 to 6 carbon atoms; n and $R^3$ are defined as above and the connection from the oxygen to the anilino moiety is in the meta position.

Most preferred are those members in which $R^1$ and $R^2$ are located in the 6 and 7 positions of the benzodioxan and are defined as hydrogen, fluoro, hydroxy, alkoxy of 1 to 4 carbon atoms or alkanoyloxy of 2 to 4 carbon atoms, or together $R^1$ and $R^2$ form a methylenedioxy, ethylenedioxy or propylenedioxy ring; $R^3$ is hydrogen or alkyl of 1 to 4 carbon atoms; n is 3; $R^4$ and $R^5$ are hydrogen; the connection from the oxygen to the aniline moiety is meta, and the configuration of the benzodioxan methanamine is S. Throughout this application, the name of a product of this invention, where the absolute configuration of the benzodioxan methanamine is not indicated, is intended to embrace the R and S isomers, as well as a mixture of the R and S isomers.

The pharmaceutically acceptable salts are those derived from such organic and inorganic acids as: acetic, lactic, citric, tartaric, succinic, maleic, malonic, hydrochloric, hydrobromic, phosphoric, nitric, sulfuric, methanesulfonic, and similarly known acceptable acids.

The compounds of this invention are prepared by conventional methods. For example, the appropriately substituted benzodioxan methanamine is combined with a suitable nitrophenoxyalkyl halide in the presence of an acid scavenger such as diisopropylethylamine in a solvent such as dimethylformamide and heated at 80°-100° C. for 24 hours, followed by reduction of the nitro group with hydrogen over palladium on carbon (1). Alternatively, a benzodioxan methylhalide or tosylate may be combined with the appropriate aminoalkoxynitrobenzene under similar conditions and heated for an extended period, again followed by reduction with hydrogen over palladium on carbon (2). The amine component may also be combined with a suitably substituted aldehyde and a reducing agent such as sodium cyanoborohydride (3), or with the appropriate acid chloride followed by reduction of the amide by an agent such as borane/THF (4). The anilino nitrogen may be alkylated, acylated, or alkyl- or arylsulfonylated by conventional methods; however, in some cases protection of the benzodioxan methanamine prior to the nitro group reduction may be desirable.

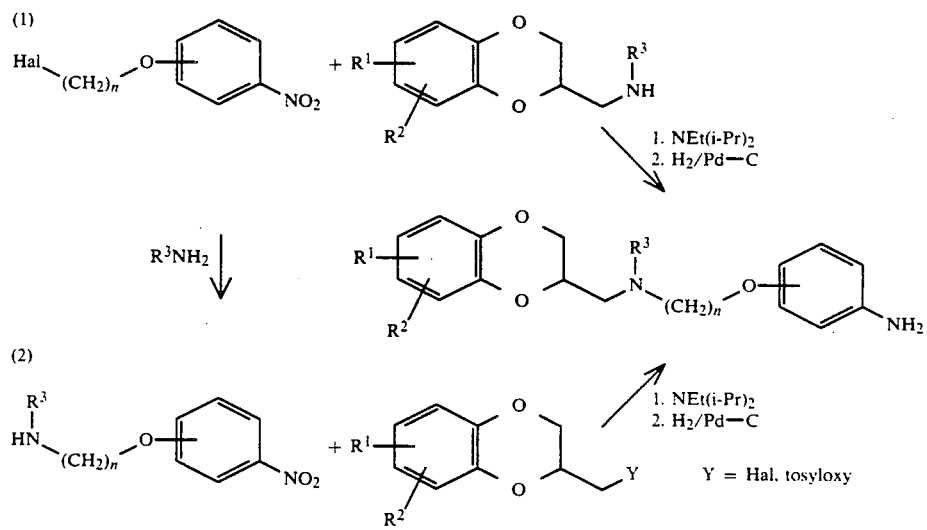

The nitrophenoxyalkyl halides appropriate for the above procedure are known compounds; the aminoalkoxynitrobenzenes may be readily prepared from them as shown above. The aldehydes and carboxylic acid chlorides appropriate to (3) and (4) may be readily prepared by one schooled in the art. The benzodioxan methanamines themselves are known compounds, or they can readily be derived from the appropriate salicylaldehyde by the procedure illustrated below. The benzodioxan methanamines may be resolved into their enantiomers by conventional methods or, preferably, they may be prepared directly by substitution of (2R)-(−)-glycidyl 3-nitrobenzenesulfonate (for the S benzodioxan methanamine) or (2S)-(+)-glycidyl 3-nitrobenzenesulfonate (for the R enantiomer) in place of epichlorohydrin in the procedure below.

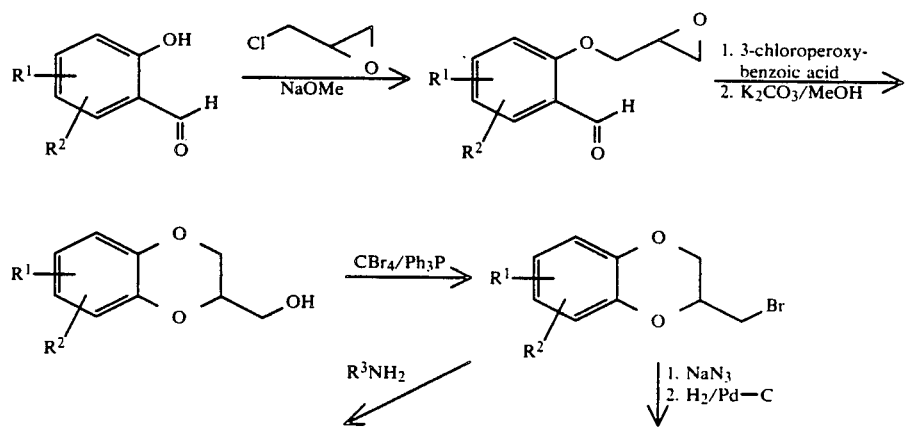

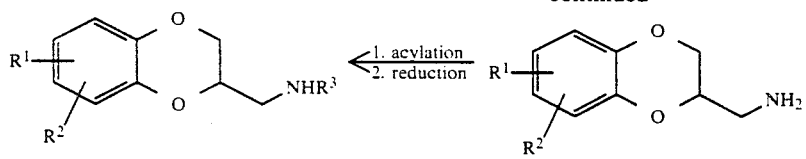

The compound of this invention are dopamine autoreceptor agonists; that is, they serve to modulate the synthesis and release of the neurotransmitter dopamine. They are thus useful for treatment of disorders of the dopaminergic system, such as schizophrenia, Parkinson's disease and Tourette's syndrome. Such agents are partial agonists at the postsynaptic dopamine $D_2$ receptor and are consequently of use in the treatment of drug addiction. Certain of the compounds of the invention also possess high affinity for serotonin 5-$HT_{1A}$ receptors and consequently, like the serotonergic agent buspirone, they are useful as antidepressant and anxiolytic agents for the treatment of a variety of central nervous system disorders such as depression, anxiety, sleep and eating disorders, sexual dysfunction, and related problems.

The effect of the compounds of the invention on the synthesis of dopamine was established by the method of Walters and Roth, Naunyn-Schmiedeberg's Arch. Pharmacol. 296:5-14, 1976, in which rats (male, Sprague-Dawley, Charles River, 200-350 g) were administered vehicle or test drug ten minutes prior to the administration of gamma butyrolactone (GBL; 750 mg/kg, ip to inhibit dopaminergic impulse flow) and 20 minutes prior to NSD-1015 (100 mg/kg, ip to prevent the conversion of dopa to dopamine). Thirty minutes after NSD-1015 all rats were decapitated and the nucleus accumbens and the striatum were removed for analysis. Following perchloric acid extraction of the tissue, the extracts were placed over alumina columns to collect and concentrate dopa and other catechols. This eluate was then subjected to HPLC analysis using electrochemical detection to quantify the levels of dopa present. Dopamine autoreceptor agonists, under the conditions used above, inhibit dopa accumulation. The results of this testing with compounds representative of this invention are reported below as % inhibition of dopa accumulation at 10 mg/kg, sc in either limbic (L) or striatal (S) brain tissue.

The antipsychotic activity of the compounds of the invention was further established by a determination of the compounds' ability to reduce mouse locomotor activity according to the method of Martin and Bendensky, J. Pharmacol. Exp. Therap. 229:706-711, 1984, in which mice (male, CF-1, Charles River, 20-30 g) were injected with vehicle or various doses of each drug and locomotor activity was measured for 30 minutes using automated infrared activity monitors (Omnitech—8×8 inch open field) located in a darkened room. $ED_{50}$'s were calculated from the horizontal activity counts collected from 10 to 20 minutes after dosing using a nonlinear regression analysis with inverse prediction. The results of this test with compounds of the invention are reported below.

Affinity for the dopamine $D_2$ receptor was established by the standard experimental test procedure of Fields, et al., Brain Res., 136, 578 (1977) and Yamamura et al., eds., Neurotransmitter Receptor Binding, Raven Press, N.Y. (1978) wherein homogenized limbic brain tissue is incubated with $^3$H-spiroperidol and various concentrations of test compound, filtered and washed and shaken with Hydrofluor scintillation cocktail (National Diagnostics) and counted in a Packard 460 CD scintillation counter. The results of this testing with compounds representative of this invention are also given below.

Affinity for the serotonin 5-$HT_{1A}$ receptor was established by testing the claimed compound's ability to displace [$^3$H]8-OHDPAT (dipropylaminotetralin) from the 5-$HT_{1A}$ serotonin receptor following the procedure of Hall et al., J. Neurochem. 44, 1685 (1985). This procedure is employed to analogize this property of the claimed compounds with that of buspirone, which is a standard for anxiolytic activity, and, like the compounds of this invention, displays potent affinity for the 5-$HT_{1A}$ serotonin receptor subtype. The anxiolytic activity of buspirone is believed to be, at least partially, due to its 5-$HT_{1A}$ receptor affinity (Vander Maclen et al., Eur. J. Pharmacol. 1986, 129 (1-2) 133-130).

The results of the standard experimental test procedures described in the preceding four paragraphs were as follows:

| Compound | Dopa Accumulation (% inhib. @ 10 mg/kg; sc) | Hypo-locomotion ($ED_{50}$ mg/kg, ip) | Receptor Affinities ($IC_{50}$ (nM) or % @ ( ) μM) | |
|---|---|---|---|---|
| | | | $D_2$ | 5-$HT_{1A}$ |
| Example 1 | 33 (L)/46 (S) | 0.38 | 525 nM | 4 nM |
| Example 2 | −22 (L) | | | |
| Example 3 | 64 (L)/66 (S) | 0.16/0.15 | 51 nM | 8 nM |
| Example 4 | 70 (L)/71 (S) | 0.08 | 50/45 nM | 15 nM |
| Example 5 | 31 (L)/30 (S) | | | |
| Example 6 | 23 (L)/30 (S) | | | |
| Example 7 | 27 (L)/19 (S) | 1.34 | 70% (1.0) | 72 nM |
| Example 8 | 42.9 (L) | | 48% (1.0) | 95% (0.1) |
| Example 9 | | 0.19 | | 100% (0.1) |
| Example 10 | 70.9 (L) | 1.8 | | 54% (0.1) |
| Example 11 | 13.0 (L) | | | |
| Example 12 | 17.4 (L) | | | |
| Example 13 | 9.1 (L) | | | |
| Example 14 | 53.7 (L) | | | |
| Example 15 | 7.6 (L) | | | |
| Example 16 | 59.9 (L) | 1.4 | | 87% (0.1) |
| Example 17 | 28 (L) | | | |
| Example 19 | 21 (L) | | | |

Hence, the compounds of this invention have a pronounced effect on the synthesis of the neurotransmitter dopamine and thus are useful in the treatment of dopaminergic disorders such as schizophrenia, Parkinson's disease, Tourette's syndrome and drug addiction. Certain compounds also demonstrated high affinity for both the serotonin 5-$HT_{1A}$ and dopamine $D_2$ receptor subtypes, and are therefore useful in the treatment of multi-CNS disorders amenable to treatment with antipsychotic, antidepressant and anxiolytic agents. As such, the compounds of this invention are useful in relieving the symptoms of anxiety, depression and various psychoses by administration, orally or parenterally to a patient in need thereof.

Applicable solid carriers can include one or more substances which may also act as flavoring agents, lubricants, solubilizers, suspending agents, fillers, glidants, compression aids, binders or tablet-disintegrating agents or an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers may be used in preparing solutions, suspensions, emulsions, syrups and elixirs. The active ingredient of this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above e.g. cellulose derivatives, preferably sodium carboxymethyl cellulose solution), alcohols (including monohydric alcohols and polyhydric alcohols e.g. glycols) and their derivatives, and oils (e.g. fractionated coconut oil and arachis oil). For parenteral administration the carrier can also be an oily ester such as ethyl oleate and isopropyl myristate. Sterile liquid carriers are used in sterile liquid form compositions for parenteral administration.

Liquid pharmaceutical compositions which are sterile solutions or suspensions can be utilized by, for example, intramuscular, intraperitoneal or subcutaneous injection. Sterile solutions can also be administered intravenously. Oral administration may be either liquid or solid composition form.

Preferably the pharmaceutical composition is in unit dosage form, e.g. as tablets or capsules. In such form, the composition is sub-divided in unit dose containing appropriate quantities of the active ingredient; the unit dosage forms can be packaged compositions, for example packeted powders, vials, ampoules, prefilled syringes or sachets containing liquids. The unit dosage form can be, for example, a capsule or tablet itself, or it can be the appropriate number of any such compositions in package form.

The dosage to be used in the treatment of a specific psychosis, state of depression or anxiety must be subjectively determined by the attending physician. The variables involved include the specific psychosis, degree of depression or state of anxiety and the size, age and response pattern of the patient.

The following examples illustrate the production of representative compounds of this invention.

EXAMPLE 1

N-[3-(3-Aminophenoxy)propyl]-2,3-dihydro-1,4-benzodioxin-2-methanamine 2,3-Dihydro-1,4-benzodioxin-2-methanamine (2.52 g, 15.3 mmole), 3-(3-nitrophenoxy)propyl chloride (2.99 g, 13.9 mmole), diisopropylethylamine (13.75 ml, 79 mmole) and sodium iodide (2.31 g, 15.4 mmole) were combined in 200 ml of DMF and heated at 95° C. for 18.5 hours under a nitrogen atmosphere. The solvent was then removed in vacuum and the residue was column chromatographed on silica gel using 1% methanol/dichloromethane as eluant. The product-containing fractions (Rf=0.75 on silica gel tlc with 5% methanol/dichloromethane) were combined and concentrated in vacuum to give 2.46 g of a brown oil. This oil was dissolved in 125 ml of methanol and 0.75 g of 10% palladium on carbon added, along with 2 ml of 4 N isopropanolic HCl. The mixture was hydrogenated at 50 psi on a Parr apparatus for 4 hours. The mixture was filtered through celite, concentrated in vacuum and the residue crystallized from isopropanol with another addition of 4 N HCl/isopropanol to give 1.63 g of title compound as a gray solid, dihydrochloride, m.p. 223°-228° C.

Elemental Analysis for: $C_{18}H_{22}N_2O_3 \cdot 2$ HCl; Calcd: C, 55.82; H, 6.25; N, 7.23. Found: C, 55.97; H, 6.34; N, 7.31.

EXAMPLE 2

N-[3-(3-Aminophenoxy)propyl]-2,3-dihydro-5-methoxy-1,4-benzodioxin-2-methanamine 2,3-Dihydro-5-methoxy-1,4-benzodioxin-2-methanamine hydrochloride (2.21 g, 9.54 mmole), 3-(3-nitrophenoxy)propyl chloride (1.95 g, 9.76 mmole), diisopropylethylamine (6.8 ml, 39 mmole) and sodium iodide (7.35 g, 49 mmole) were combined in 100 ml of DMF and heated at 80°-100° C. for 3 days under a nitrogen atmosphere. The solvent was then removed in vacuum and the residue was column chromatographed on silica gel using first 30% ethyl acetate/petty ether and then 2.5% methanol/dichloromethane as eluant. The product-containing fractions were combined and concentrated in vacuum to give 2.04 g of nitrophenoxyalkyl derivative. This was dissolved in 200 ml of methanol/water, 0.36 g of 5% palladium on carbon and 3 ml of 4N isopropanolic HCl added and the mixture hydrogenated at 50 psi on a Parr apparatus for 3 hours. The mixture was filtered through celite, concentrated in vacuum, and the residue crystallized from isopropanol to give 1.45 g of title compound as a white solid, dihydrochloride, quarter hydrate, m.p. 230°-236° C.

Elemental Analysis for: $C_{19}H_{24}N_2O_4 \cdot 2$ HCl·¼ H$_2$O; Calcd: C, 54.10; H, 6.33; N, 6.64. Found: C, 54.47; H, 6.50; N, 6.32.

EXAMPLE 3

N-[3-(3-Aminophenoxy)propyl]-2,3-dihydro-7-hydroxy-1,4-benzodioxin-2-methanamine 2,3-Dihydro-7-benzyloxy-1,4-benzodioxin-2-methanamine (1.49 g, 5.49 mmole), 3-(3-nitrophenoxy)-propyl chloride (1.13 g, 5.66 mmole), diisopropylethylamine (4.0 ml, 23 mmole) and sodium iodide (4.18 g, 27.9 mmole) were combined in 150 ml of DMF and heated at 80°-100° C. for 24 hours under a nitrogen atmosphere. The solvent was then removed in vacuum and the residue was column chromatographed on silica gel using a gradient elution commencing with dichloromethane and ending with 1.5% methanol/dichloromethane as eluant. The product-containing fractions were combined and concentrated in vacuum to give 0.82 g of nitrophenoxyalkyl derivative as a brown oil. This was dissolved in 75 ml of ethanol, and 0.20 g of 5% palladium on carbon added and the mixture hydrogenated at 50 psi on a Parr apparatus for 24 hours. The mixture was filtered through celite, concentrated in vacuum, and the residue crystallized from 50 ml of isopropanol with the addition of 3 ml of 4N HCl/isopropanol to give 0.47 g of title compound as a beige solid, dihydrochloride, quarter hydrate, m.p. 173° C.

Elemental Analysis for: $C_{18}H_{22}N_2O_4 \cdot 2$ HCl$\cdot\frac{1}{4}$ H$_2$O; Calcd: C, 53.01; H, 6.05; N, 6.87. Found: C, 53.15; H, 6.01; N, 6.56.

EXAMPLE 4

(S)-N-[3-(3-Aminophenoxy)propyl]-2,3-dihydro-7-hydroxy-1,4-benzodioxin-2-methanamine (S)-2,3-Dihydro-7-hydroxy-1,4-benzodioxin-2-methanamine (2.37 g, 13.1 mmole), 3-(3-nitrophenoxy)-propyl chloride (2.18 g, 10.1 mmole), diisopropylethylamine (9.0 ml, 52 mmole) and sodium iodide (2.84 g, 19 mmole) were combined in 175 ml of DMF and heated at 97° C. for 25 hours under a nitrogen atmosphere. The solvent was then removed in vacuum and the residue was column chromatographed on silica gel using a gradient elution commencing with 0.5% methanol/dichloromethane and ending with 1.5% methanol/dichloromethane as eluant. The product-containing fractions were combined and concentrated in vacuum to give 2.87 g of nitrophenoxyalkyl derivative as a purple semi-solid. This was dissolved in 125 ml of ethanol, and 0.30 g of 10% palladium on carbon added and the mixture hydrogenated at 50 psi on a Parr apparatus for 24 hours. The mixture was filtered through celite, concentrated in vacuum, and the residue column chromatographed on silica gel using 1% methanol/dichloromethane. The product-containing fractions (Rf=0.26 with 5% methanol/dichloromethane on silica gel) were combined and evaporated in vacuum and the residue crystallized from isopropanol with the addition of 4 ml of 4 N HCl/isopropanol to give 1.1 g of title compound as a tan solid, monohydrochloride, m.p. 182°-185° C., $[\alpha]_D^{25} = -43.4°$.

Elemental Analysis for: $C_{18}H_{20}N_2O_4 \cdot 2$ HCl; Calcd: C, 53.61; H, 6.00; N, 6.95. Found: C, 53.46; H, 6.13; N, 6.83.

EXAMPLE 5

N-[3-(3-Aminophenoxy)propyl]-2,3-dihydro-6-hydroxy-1,4-benzodioxin-2-methanamine 2,3-Dihydro-7-hydroxy-1,4-benzodioxin-2-methanamine (2.37 g, 13.1 mmole), 3-(3-nitrophenoxy)propyl chloride (2.20 g, 10.2 mmole), diisopropylethylamine (9.0 ml, 53.3 mmole) and sodium iodide (2.81 g, 18.8 mmole) were combined in 175 ml of DMF and heated at 80°-100° C. for 2 days under a nitrogen atmosphere. The solvent was then removed in vacuum and the residue was column chromatographed on silica gel using a gradient elution commencing with 0.5% methanol/dichloromethane and ending with 1.5% methanol/dichloromethane as eluant. The product-containing fractions were combined and concentrated in vacuum to give 3.70 g of nitrophenoxyalkyl derivative as a brown oil. 3.19 g of this material was dissolved in 75 ml of ethanol, and 0.50 g of 10% palladium on carbon and 7.0 ml of 4N HCl/isopropanol added and the mixture hydrogenated at 50 psi on a Parr apparatus for 7 days, with two more additions of catalysts on days 2 and 6. The mixture was filtered through celite, concentrated in vacuum, and the residue crystallized from 75 ml of isopropanol to give 0.95 g of title compound as a beige solid, dihydrochloride, half hydrate, m.p. 242°-245° C.

Elemental Analysis for: $C_{18}H_{22}N_2O_4 \cdot 2$ HCl$\cdot\frac{1}{2}$ H$_2$O; Calcd: C, 52.44; H, 6.11; N, 6.79. Found: C, 52.67; H, 6.06; N, 6.80.

EXAMPLE 6

N-[3-(3-Aminophenoxy)propyl]-2,3-dihydro-5-hydroxy-1,4-benzodioxin-2-methanamine N-[3-(3-Aminophenoxy)propyl]-2,3-dihydro-5-methoxy-1,4-benzodioxin-2-methanamine dihydrochloride quarter hydrate (0.79 g, 1.9 mmole), prepared in Example 2 above, was dissolved in 26.5 ml of 48% HBr and refluxed under nitrogen for 23 hours. Upon cooling, the mixture was diluted to 250 ml with water and carefully neutralized with solid sodium bicarbonate. It was then extracted with two 200 ml portions of 3:1 dichloromethane/isopropanol and the combined extracts were washed with saturated aqueous sodium chloride, dried over magnesium sulfate, filtered and concentrated to dryness in vacuum. The residue was column chromatographed on silica gel using 5% methanol/dichloromethane to which 1 ml/liter aqueous ammonia had been added. The product-containing fractions were combined, concentrated in vacuum, and the residue crystallized from 20 ml of isopropanol with the addition of 4 ml 4N HCl/isopropanol to give 0.33 g of the title compound (m.p. 183°-190° C.) as a beige solid, dihydrochloride.

Elemental Analysis for: $C_{18}H_{22}N_2O_4 \cdot 2$ HCl; Calcd: C, 53.61; H, 6.00; N, 6.95. Found: C, 53.83; H, 6.33; N, 6.55.

EXAMPLE 7

(R)-N-[3-(3-Aminophenoxy)propyl]-2,3-dihydro-7-hydroxy-1,4-benzodioxin-2-methanamine (R)-2,3-Dihydro-7-hydroxy-1,4-benzodioxin-2-methanamine (5.63 g, 31.0 mmole), 3-(3-nitrophenoxy)-propyl chloride (6.27 g, 29.1 mmole), diisopropylethylamine (15.5 ml, 89 mmole) and sodium iodide (4.25 g, 28.4 mmole) were combined in 200 ml of DMF and heated at 77° C. for 24 hours under a nitrogen atmosphere. The solvent was then removed in vacuum and the residue was column chromatographed on silica gel using a gradient elution commencing with 0.5% methanol/dichloromethane and ending with 2.5% methanol/dichloromethane as eluant. The product-containing fractions were combined and concentrated in vacuum to give 3.29 g of nitrophenoxyalkyl derivative as a light brown oil. This was dissolved in 100 ml of ethanol, and 0.75 g of 10% palladium on carbon added and the mixture hydrogenated at 50 psi on a Parr apparatus for 3 days. The mixture was filtered through celite, concentrated in vacuum, and the residue crystallized from 70 ml of isopropanol with the addition of 10 ml of 4N HCl/IPA to give 2.13 g of title compound as a tan solid, dihydrochloride, m.p. 181°-190° C., $[\alpha]_D^{25} = +42.7°$ (MeOH).

Elemental Analysis for: $C_{18}H_{22}N_2O_4 \cdot 2$ HCl; Calcd: C, 53.61; H, 6.00; N, 6.95. Found: C, 53.36; H, 5.77; N, 7.00.

EXAMPLE 8

N-[3-(3-Aminophenoxy)propyl]-2,3-dihydro-7-methoxy-1,4-benzodioxin-2-methanamine 2,3-Dihydro-7-methoxy-1,4-benzodioxin-2-methanamine (3.8 g, 20 mmole), 3-(3-nitrophenoxy)propyl bromide (5.2 g, 20 mmole), and diisopropylethylamine (2.6 g, 20 mmole) were combined in 200 ml of DMF and heated at 100° C. for 24 hours under a nitrogen atmosphere. The solvent was then removed in vacuum and the residue column chromatographed on 100 g of silica gel using first dichloromethane, then chloroform, and finally 2% methanol/chloroform as eluant. The product-containing fractions were combined and concentrated in vacuum to give 3.25 g of a yellow solid. A portion (1.25 g, 3.3 mmole) of this material was dissolved in 200 ml of ethanol and 0.50 g of 10% palladium on carbon added, along with 4 ml of 4N isopropanolic HCl. The mixture was hydrogenated at 50 psi on a Parr apparatus for 24 hours. The mixture was filtered through celite, concentrated in vacuum.and the residue crystallized from 75 ml of isopropanol to give 1.0 g of title compound as a white solid, dihydrochloride, m.p. 210°-212° C.

Elemental Analysis for: $C_{19}H_{24}N_2O_4 \cdot 2$ HCl; Calcd: C, 54.68; H, 6.28; N, 6.71. Found: C, 54.34; H, 6.10; N, 6.71.

EXAMPLE 9

(S)-N-[3-(3-Aminophenoxy)propyl]-2,3-dihydro-1,4-benzodioxin-2-methanamine (S)-2,3-Dihydro-1,4-benzodioxin-2-methanamine (3.5 g, 21 mmole), 3-(3-nitrophenoxy)propyl bromide (5.5 g, 21 mmole) and diisopropylethylamine (2.7 g, 21 mmole) were combined in 100 ml of DMF and heated at 80°-90° C. for 24 hours under a nitrogen atmosphere. The solvent was then removed in vacuum and the residue was redissolved in 350 ml of dichloromethane and washed with 250 ml portions of saturated aqueous sodium bicarbonate solution and saturated sodium chloride solution, dried over sodium sulfate, filtered and evaporated to dryness in vacuum. The residue was column chromatographed on 100 g silica gel with a gradient elution commencing with chloroform and ending with 2% methanol in chloroform. The product-containing fractions were combined and concentrated in vacuum to give 3.85 g of an orange oil. A portion (1.25 g, 3.6 mmole) of this oil was dissolved in 150 ml of methanol and 0.50 g of 10% palladium on carbon added, along with 3 ml of 4N isopropanolic HCl. The mixture was hydrogenated at 50 psi on a Parr apparatus for 24 hours. The mixture was filtered through celite and concentrated and the residue crystallized from 50 ml of isopropanol to give 1.1 g of title compound as a white solid, dihydrochloride, m.p. 245°-247° C.

Elemental Analysis for: $C_{18}H_{22}N_2O_3 \cdot 2$ HCl; Calcd: C, 55.82; H, 6.25; N, 7.23. Found: C, 55.61; H, 6.17; N, 7.10.

EXAMPLE 10

N-[3-(3-Aminophenoxy)propyl]-2,3-dihydro-6,7-methylenedioxy-1,4-benzodioxin-2-methanamine 2,3-Dihydro-6,7-methylenedioxy-1,4-benzodioxin-2-methanamine (3.59 g, 17 mmole), 3-(3-nitrophenoxy)propyl bromide (4.42 g, 17 mmole), diisopropylethylamine (14.8 ml, 85 mmole) and sodium iodide (2.80 g, 18.7 mmole) were combined in 200 ml of DMF and heated at 95° C. overnight under a nitrogen atmosphere. The solvent was then removed in vacuum and the residue triturated with hot methanol to produce a yellow solid. This was suspended in chloroform and washed with saturated aqueous sodium bicarbonate and the organic phase dried with magnesium sulfate, filtered and concentrated in vacuum. The residue was column chromatographed on silica gel using 5% methanol/chloroform as eluant. The product-containing fractions were combined and concentrated in vacuum to give 3.80 g of a yellow oil. A portion (1.8 g, 4.6 mmole) of this oil was dissolved in 50% methanol-water and 0.49 g of 10% palladium on carbon added, along with 1.15 ml of 4N isopropanolic HCl. The mixture was hydrogenated at 50 psi on a Parr apparatus overnight, filtered through celite, concentrated in vacuum and the residue recrystallized from ethanol to give 0.62 g of title compound as a gray solid, dihydrochloride, m.p. 211°-212° C.

Elemental Analysis for: $C_{19}H_{22}N_2O_5 \cdot 2$ HCl; Calcd: C, 52.91; H, 5.61; N, 6.49. Found: C, 53.10; H, 5.71; N, 6.34.

EXAMPLE 11

N-[3-(3-Aminophenoxy)propyl]-2,3-dihydro-8-methoxy-1,4-benzodioxin-2-methanamine 2,3-Dihydro-8-methoxy-1,4-benzodioxin-2-methanamine (3.8 g, 20 mmole), 3-(3-nitrophenoxy)propyl bromide (5.2 g, 20 mmole), and diisopropylethylamine (2.6 g, 20 mmole) were combined in 150 ml of DMF and heated at 80° C. for 24 hours under a nitrogen atmosphere. The solvent was then removed in vacuum and the residue column chromatographed on 100 g of silica gel using first dichloromethane, then chloroform, and finally 2% methanol/chloroform as eluant. The product-containing fractions were combined and concentrated in vacuum to give 5.5 g of a dark oil. This material was dissolved in 150 ml of methanol and 0.50 g of 10% palladium on carbon added, along with 10 ml of 4N isopropanolic HCl. The mixture was hydrogenated at 55 psi on a Parr apparatus for 24 hours. The mixture was then filtered through celite, and treated with charcoal while boiling on a hot plate. After a second filtration through celite, the mixture was brought to a boil on a hot plate, and the solvent gradually replaced with isopropanol The volume was then reduced to 75 ml and allowed to cool to give 2.2 g of title compound as a yellow solid, dihydrochloride, monohydrate, m.p. 200°-205° C.

Elemental Analysis for: $C_{19}H_{24}N_2O_4 \cdot 2$ HCl·$H_2O$; Calcd: C, 52.42; H, 6.48; N, 6.44. Found: C, 52.39; H, 6.38; N, 6.48.

EXAMPLE 12

N-[3-(3-Aminophenoxy)propyl]-2,3-dihydro-8-hydroxy-1,4-benzodioxin-2-methanamine N-[3-(3-Aminophenoxy)propyl]-2,3-dihydro-8-methoxy-1,4-benzodioxin-2-methanamine dihydrochloride hydrate (1.2 g, 2.75 mmole), prepared in Example 11 above, was dissolved in 25 ml of 48% HBr and refluxed overnight under nitrogen. The mixture was diluted with water to 300 ml, carefully neutralized with solid sodium carbonate, and twice extracted with 200 ml of 3:1 dichloromethane/isopropanol. The combined extracts were washed with saturated aqueous sodium chloride, dried over sodium sulfate, filtered and concentrated in vacuum. The residue was crystallized from 50 ml of isopropanol with the addition of 2 ml of 4N HCl/isopropanol to give 0.37 g of the title compound as a tan solid, dihydrochloride, quarter hydrate, m.p. 249°-255° C.

Elemental Analysis for: $C_{18}H_{22}N_2O_4 \cdot 2$ HCl·¼ $H_2O$; Calcd: C, 53.01; H, 6.05; N, 6.87. Found: C, 52.89; H, 6.18; N, 6.76.

EXAMPLE 13

N-[3-(3-Aminophenoxy)propyl]-2,3-dihydro-7-chloro-1,4-benzodioxin-2-methanamine 2,3-Dihydro-7-chloro-1,4-benzodioxin-2-methanamine (2.08 g, 8.81 mmole), 3-(3-nitrophenoxy)propyl bromide (2.09 g, 8.04 mmole) and diisopropylethylamine (7.0 ml, 40.2 mmole) were combined in 200 ml of DMF and heated at 80° C. for 3 days under a nitrogen atmosphere. The solvent was then removed in vacuum and the residue was column chromatographed on silica gel using 50 to 60% ethyl acetate/hexane as eluant. The product-containing fractions were combined and concentrated in vacuum to give 0.40 g of nitrophenoxyalkyl derivative. This was dissolved in 100 ml of methanol and 0.11 g of 10% palladium on carbon added, along with 2 ml of 4N isopropanolic HCl. The mixture was hydrogenated at 50 psi on a Parr apparatus for 1 hours. The mixture was filtered through celite, concentrated in vacuum and the residue twice recrystallized from isopropanol to give 0.13 g of title compound as a white solid, dihydrochloride, three quarter hydrate, m.p. 216°-226° C.

Elemental Analysis for: $C_{18}H_{21}ClN_2O_3 \cdot 2$ HCl$\cdot \frac{3}{4}$ H$_2$O; Calcd: C, 49.67; H, 5.67; N, 6.43. Found: C, 49.66; H, 5.99; N, 6.01.

EXAMPLE 14

N-[3-(3-Aminophenoxy)propyl]-2,3-dihydro-6,7-dimethoxy-1,4-benzodioxin-2-methanamine 2,3-Dihydro-6,7-dimethoxy-1,4-benzodioxin-2-methanamine (6.23 g, 28 mmole), 3-(3-nitrophenoxy)propyl bromide (7.28 g, 28 mmole) and diisopropylethylamine (24.4 ml, 0.14 mole) were combined in 200 ml of DMF and heated at 95° C. overnight under a nitrogen atmosphere. The solvent was then removed in vacuum and the residue dissolved in chloroform and washed with saturated aqueous sodium bicarbonate, dried over magnesium sulfate, filtered and concentrated in vacuum. The residue was column chromatographed on silica gel using 5% methanol/chloroform as eluant. The product-containing fractions were combined and concentrated in vacuum to give 5.86 g of a yellow solid. A portion (2.0 g, 4.9 mmole) of this solid was dissolved in ethanol (200 ml) and 1.0 g of 10% palladium on carbon added, along with 3.0 ml of 4N isopropanolic HCl. The mixture was hydrogenated at 50 psi on a Parr apparatus overnight, filtered through celite, concentrated in vacuum to a white solid and recrystallized from methanol/isopropanol to give 2.06 g of title compound as an off-white solid, dihydrochloride, m.p. 220°-222° C.

Elemental Analysis for: $C_{20}H_{26}N_2O_5 \cdot 2$ HCl; Calcd: C, 53.70; H, 6.31; N, 6.26. Found: C, 53.61; H, 6.49; N, 6.18.

EXAMPLE 15

N-[3-(3-Aminophenoxy)propyl]-2,3-dihydro-5,6-dimethoxy-1,4-benzodioxin-2-methanamine 2,3-Dihydro-5,6-dimethoxy-1,4-benzodioxin-2-methanamine (3.83 g, 17 mmole), 3-(3-nitrophenoxy)propyl bromide (4.42 g, 17 mmole) and diisopropylethylamine (14.8 ml, 85 mmole) were combined in 200 ml of DMF and heated at 95° C. overnight under a nitrogen atmosphere. The solvent was then removed in vacuum and the residue dissolved in chloroform and washed with saturated aqueous sodium bicarbonate, dried over magnesium sulfate, filtered and concentrated in vacuum. The residue was column chromatographed on silica gel using 5% methanol/chloroform as eluant. The product-containing fractions were combined and concentrated in vacuum to give 3.53 g of a yellow oil. A portion (2.0 g, 4.9 mmole) of this solid was dissolved in ethanol (200 ml) and 1.0 g of 10% palladium on carbon added, along with 4N isopropanolic HCl (to pH 3). The mixture was hydrogenated at 50 psi on a Parr apparatus overnight, filtered through celite, concentrated in vacuum to a white solid and recrystallized from methanol/isopropanol to give 1.77 g of title compound as a white solid, dihydrochloride, quarter hydrate, m.p. 205°-207° C.

Elemental Analysis for: $C_{20}H_{26}N_2O_5 \cdot 2$ HCl$\cdot \frac{1}{4}$ H$_2$O; Calcd: C, 53.16; H, 6.36; N, 6.20. Found: C, 52.86; H, 6.35; N, 6.08.

EXAMPLE 16

N-[3-(3-Aminophenoxy)propyl]-2,3-dihydro-7-fluoro-1,4-benzodioxin-2-methanamine 2,3-Dihydro-7-fluoro-1,4-benzodioxin-2-methanamine (4.5 g, 24 mmole), 3-(3-nitrophenoxy)propyl bromide (6.24 g, 24 mmole) and diisopropylethylamine (20.1 ml, 0.12 mole) were combined in 200 ml of DMF and heated at 95° C. overnight under a nitrogen atmosphere. The solvent was then removed in vacuum and the residue dissolved in chloroform and washed with saturated aqueous sodium bicarbonate, dried over magnesium sulfate, filtered and concentrated in vacuum. The residue was column chromatographed on silica gel using 5% methanol/chloroform as eluant. The product-containing fractions were combined and concentrated in vacuum to give 3.0 g of a dark yellow oil. A portion (2.0 g, 5.5 mmole) of this was dissolved in ethanol (100 ml) and 1.0 g of 10% palladium on carbon added, along with 4N isopropanolic HCl (to pH 3). The mixture was hydrogenated at 50 psi on a Parr apparatus overnight, filtered through celite, concentrated in vacuum to an off-white solid and column chromatographed on silica gel with 5% methanol/chloroform (with 1 ml/liter aqueous ammonia added). The product-containing fractions were combined and evaporated in vacuum and recrystallized from methanol/isopropanol with addition of 4N HCl/isopropanol; however, the resulting solid proved to be contaminated with ammonium chloride. The product was reconverted to the free base by passing a methanol solution through Amberlite, IRA-400 (OH) ion exchange resin and concentration in vacuum. After overnight storage in vacuum, the residue was once again crystallized from methanol/isopropanol with addition of 4N HCl/isopropanol to give 0.32 g of title compound as an tan solid, dihydrochloride, half hydrate, m.p. 209°-212° C.

Elemental Analysis for: $C_{18}H_{21}FN_2O_3 \cdot 2$ HCl$\cdot \frac{1}{2}$ H$_2$O; Calcd: C, 52.18; H, 5.84; N, 6.76. Found: C, 52.09; H, 5.62; N, 6.56.

EXAMPLE 17

(S)-N-[3-(3-Aminophenoxy)propyl]-2,3-dihydro-7-methoxy-1,4-benzodioxin-2-methanamine (S)-2,3-Dihydro-7-methoxy-1,4-benzodioxin-2-methanamine hydrochloride (7.42 g, 32.0 mmole), 3-(3-nitrophenoxy)propyl bromide (7.644 g, 29.4 mmole) and diisopropylethylamine (8.0 ml, 46 mmole) were combined in 300 ml of DMF and heated at 86° C. for 26 hours under a nitrogen atmosphere. The solvent was then removed in vacuum and the residue dissolved in dichloromethane and washed with saturated aqueous sodium bicarbonate and with saturated aqueous sodium chloride, dried over magnesium sulfate, filtered and concentrated in vacuum. The residue was column chromatographed on 500 g of silica gel using 70% ethyl acetate/chloroform as eluant. The product-containing fractions were combined and concentrated in vacuum to give 4.5 g of a brown oil. This was dissolved in methanol (125 ml) and 0.86 g of 10% palladium on carbon added, along with 6.0 ml of 4N isopropanolic HCl. The mixture was hydrogenated at 50 psi on a Parr apparatus overnight, filtered through celite, concentrated in vacuum. and the residue crystallized from methanol/isopropanol with a further addition of 4N isopropanolic HCl to yield 2.07 g of the title compound as a white solid, dihydrochloride, half hydrate, m.p. 204°–208° C.

Elemental Analysis for: $C_{19}H_{24}N_2O_4 \cdot 2$ HCl$\cdot\frac{1}{2}H_2O$; Calcd: C, 53.53; H, 6.38; N, 6.57. Found: C, 53.47; H, 6.14; N, 6.43.

EXAMPLE 18

N-[3-(3-Aminophenoxy)propyl]-2,3-dihydro-6,8-dimethoxy-1,4-benzodioxin-2-methanamine 2,3-Dihydro-6,8-dimethoxy-1,4-benzodioxin-2-methanamine hydrochloride (6.24 g, 23.8 mmole), 3-(3-nitrophenoxy)propyl bromide (6.51 g, 21.4 mmole) and diisopropylethylamine (4.5 ml, 26 mmole) were combined in 315 ml of DMF and heated at 80°–100° C. for 24 hours under a nitrogen atmosphere. The solvent was then removed in vacuum and the residue dissolved in dichloromethane and washed with 300 ml of saturated aqueous sodium bicarbonate, dried over magnesium sulfate, filtered and concentrated in vacuum. The residue was column chromatographed on 300 g of silica gel using first 30% ethyl acetate/dichloromethane and then 1% methanol/dichloromethane as eluant. The product-containing fractions were combined and concentrated in vacuum to give 4.6 g of oil. This was dissolved in methanol (175 ml) and 0.7 g of 10% palladium on carbon added, along with 6.0 ml of 4N isopropanolic HCl. The mixture was hydrogenated at 42 psi on a Parr apparatus overnight, filtered through celite, concentrated in vacuum and the residue crystallized from methanol/isopropanol with a further addition of 4N isopropanolic HCl to yield 1.14 g of the title compound as a white solid, dihydrochloride, half hydrate, m.p. 123°–128° C.

Elemental Analysis for: $C_{20}H_{26}N_2O_5 \cdot 2$ HCl$\cdot\frac{1}{2}$ $H_2O$; Calcd: C, 52.63; H, 6.40; N, 6.13. Found: C, 52.63; H, 6.37; N, 6.14.

EXAMPLE 19

N-[3-(3-Aminophenoxy)propyl]-2,3-dihydro-7-hydroxy-8-methyl-1,4-benzodioxin-2-methanamine 2,3-Dihydro-7-hydroxy-8-methyl-1,4-benzodioxin-2-methanamine (0.70 g, 3.6 mmole), 3-(3-nitrophenoxy)propyl bromide (0.94 g, 3.6 mmole) and diisopropylethylamine (0.47 g, 3.6 mmole) were combined in 50 ml of DMF and heated at 80° C. for 24 hrs. under a nitrogen atmosphere. The solvent was then removed in vacuum and the residue dissolved in chloroform and washed with saturated aqueous sodium bicarbonate, dried over magnesium sulfate, filtered and concentrated in vacuum. The residue was column chromatographed on silica gel using first chloroform and then 2% methanol/chloroform as eluant. The product-containing fractions were combined and concentrated in vacuum to give a dark yellow oil. This was dissolved in methanol (100 ml) and 0.5 g of 10% palladium on carbon added, along with 5 ml of 4N isopropanolic HCl. The mixture was hydrogenated at 50 psi on a Parr apparatus overnight, filtered through celite, concentrated in vacuum. to an off-white solid and column chromatographed on silica gel with 5% methanol/chloroform (with 1 ml/liter aqueous ammonia added). The product-containing fractions were combined and evaporated in vacuum and recrystallized from isopropanol with addition of 4N HCl/IPA to give 0.32 g of title compound as a yellow solid, dihydrochloride, hydrate, isopropanol solvate, m.p. 156° C. (d).

Elemental Analysis for: $C_{19}H_{24}N_2O_4 \cdot 2$ HCl$\cdot H_2O \cdot \frac{1}{4}C_3H_8O$; Calcd: C, 54.21; H, 7.45; N, 5.75. Found: C, 54.62; H, 7.07; N, 5.58.

What is claimed is:

1. A compound of the formula:

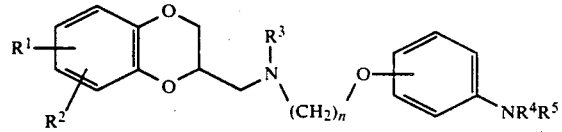

wherein

R$^1$ and R$^2$ are, independently, hydrogen, alkyl of 1 to 6 carbon atoms, alkoxy of 1 to 6 carbon atoms, aralkoxy of 7 to 12 carbon atoms, alkanoyloxy of 2 to 6 carbon atoms, hydroxy, halo, amino, mono- or dialkylamino in which each alkyl group contains from 1 to 6 carbon atoms, alkanamido of 2 to 6 carbon atoms, or sulfonamido, or R$^1$ and R$^2$ together form methylenedioxy, ethylenedioxy, or propylenedioxy;

R$^3$ is hydrogen or alkyl of 1 to 6 carbon atoms;

n is one of the integers 2, 3 or 4;

R$^4$ and R$^5$ are, independently, hydrogen, alkyl of 1 to 6 carbon atoms, cycloalkyl of 4 to 7 carbon atoms, alkanoyl of 2 to 6 carbon atoms, aroyl of 7 to 12 carbon atoms, alkylsulfonyl of 1 to 6 carbon atoms or arylsulfonyl of 6 to 10 carbon atoms, or R$^4$ and R$^5$ together form a 3–7 membered polymethylene ring;

or a pharmaceutically acceptable salt thereof.

2. A compound of claim 1 in which R$^1$ and R$^2$ are, independently, hydrogen, fluoro, hydroxy, alkoxy of 1 to 6 carbon atoms or alkanoyloxy of 2 to 6 carbon atoms, or together form a methylenedioxy, ethylenedioxy or propylenedioxy ring; R$^4$ and R$^5$ are, independently, hydrogen or alkyl of 1 to 6 carbon atoms; and the bond between oxygen and the anilino moiety is in meta position.

3. A compound of claim 1 of the formula:

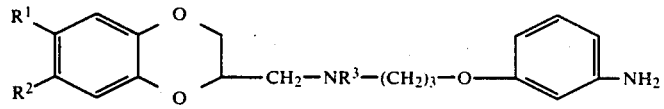

in which

R¹ and R² are, independently, hydrogen, fluoro, hydroxy, alkoxy of 1 to 4 carbon atoms, alkanoyloxy of 2 to 4 carbon atoms or together form alkylenedioxy of 1 to 3 carbon atoms;

R³ is hydrogen or alkyl of 1 to 4 carbon atoms;

or a pharmaceutically acceptable salt thereof, where the benzodioxan methanamine moiety is in the S-configuration.

4. The compound of claim 1 which is N-[3-(3-aminophenoxy)propyl]-2,3-dihydro-1,4-benzodioxin-2-methanamine, or a pharmaceutically acceptable salt thereof.

5. The compound of claim 1 which is N-[3-(3-aminophenoxy)propyl]-2,3-dihydro-5-methoxy-1,4-benzodioxin-2-methanamine, or a pharmaceutically acceptable salt thereof.

6. The compound of claim 1 which is N-[3-(3-aminophenoxy)propyl]-2,3-dihydro-7-hydroxy-1,4-benzodioxin-2-methanamine, or a pharmaceutically acceptable salt thereof.

7. The compound of claim 1 which is N-[3-(3-aminophenoxy)propyl]-2,3-dihydro-6-hydroxy-1,4-benzodioxin-2-methanamine, or a pharmaceutically acceptable salt thereof.

8. The compound of claim 1 which is N-[3-(3-aminophenoxy)propyl]-2,3-dihydro-5-hydroxy-1,4-benzodioxin-2-methanamine, or a pharmaceutically acceptable salt thereof.

9. The compound of claim 1 which is N-[3-(3-aminophenoxy)propyl]-2,3-dihydro-7-methoxy-1,4-benzodioxin-2-methanamine, or a pharmaceutically acceptable salt thereof.

10. The compound of claim 1 which is N-[3-(3-aminophenoxy)propyl]-2,3-dihydro-6,7-methylenedioxy-1,4-benzodioxin-2-methanamine, or a pharmaceutically acceptable salt thereof.

11. The compound of claim 1 which is N-[3-(3-aminophenoxy)propyl]-2,3-dihydro-8-methoxy-1,4-benzodioxin-2-methanamine, or a pharmaceutically acceptable salt thereof.

12. The compound of claim 1 which is N-[3-(3-aminophenoxy)propyl]-2,3-dihydro-8-hydroxy-1,4-benzodioxin-2-methanamine, or a pharmaceutically acceptable salt thereof.

13. The compound of claim 1 which is N-[3-(3-aminophenoxy)propyl]-2,3-dihydro-7-chloro-1,4-benzodioxin-2-methanamine, or a pharmaceutically acceptable salt thereof.

14. The compound of claim 1 which is N-[3-(3-aminophenoxy)propyl]-2,3-dihydro-6,7-dimethoxy-1,4-benzodioxin-2-methanamine, or a pharmaceutically acceptable salt thereof.

15. The compound of claim 1 which is N-[3-(3-aminophenoxy)propyl]-2,3-dihydro-5,6-dimethoxy-1,4-benzodioxin-2-methanamine, or a pharmaceutically acceptable salt thereof.

16. The compound of claim 1 which is N-[3-(3-aminophenoxy)propyl]-2,3-dihydro-7-fluoro-1,4-benzodioxin-2-methanamine, or a pharmaceutically acceptable salt thereof.

17. The compound of claim 1 which is N-[3-(3-aminophenoxy)propyl]-2,3-dihydro-6,8-dimethoxy-1,4-benzodioxin-2-methanamine, or a pharmaceutically acceptable salt thereof.

18. The compound of claim 1 which is N-[3-(3-aminophenoxy)propyl]-2,3-dihydro-7-hydroxy-8-methyl-1,4-benzodioxin-2-methanamine, or a pharmaceutically acceptable salt thereof.

19. A process for alleviating the symptoms of psychoses, depression or anxiety which comprises administering, orally or parenterally, to a patient in need thereof, an antipsychotic, antidepressant or anxiolytic amount of a compound of the formula:

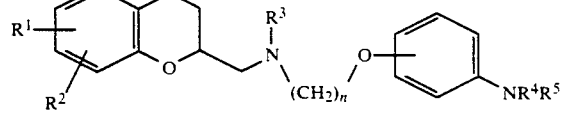

wherein

R¹ and R² are, independently, hydrogen, alkyl of 1 to 6 carbon atoms, alkoxy of 1 to 6 carbon atoms, aralkoxy of 7 to 12 carbon atoms, alkanoyloxy of 2 to 6 carbon atoms, hydroxy, halo, amino, mono- or dialkylamino in which each alkyl group contains from 1 to 6 carbon atoms, alkanamido of 2 to 6 carbon atoms, or sulfonamido, or R¹ and R² together form methylenedioxy, ethylenedioxy, or propylenedioxy;

R³ is hydrogen or alkyl of 1 to 6 carbon atoms;

n is one of the integers 2, 3 or 4;

R⁴ and R⁵ are, independently, hydrogen, alkyl of 1 to 6 carbon atoms, cycloalkyl of 4 to 7 carbon atoms, alkanoyl of 2 to 6 carbon atoms, aroyl of 7 to 12 carbon atoms, alkylsulfonyl of 1 to 6 carbon atoms or arylsulfonyl of 6 to 10 carbon atoms, or R⁴ and R⁵ together form a 3-7 membered polymethylene ring;

or a pharmaceutically acceptable salt thereof.

* * * * *